United States Patent [19]

Kamesaran et al.

[11] 4,164,415
[45] Aug. 14, 1979

[54] BRANCHED ALKYL-2-NAPHTHALENEACETIC ACIDS AS HERBICIDES AND INSECTICIDE INTERMEDIATES

[75] Inventors: Venkataraman Kamesaran, Pennbrook, Pa.; Roger W. Addor, Pennington, N.J.

[73] Assignee: American Cyanamid Co., Stamford, Conn.

[21] Appl. No.: 673,245

[22] Filed: Apr. 2, 1976

[51] Int. Cl.$^2$ .................... A01N 9/24; C07C 63/36
[52] U.S. Cl. ............................... 71/114; 562/490
[58] Field of Search .............. 71/114; 260/515 R; 562/490

[56] References Cited

U.S. PATENT DOCUMENTS

| | | | |
|---|---|---|---|
| 2,229,948 | 1/1941 | Weil | 71/114 |
| 2,278,499 | 4/1942 | Smith et al. | 71/114 |
| 2,341,867 | 6/1939 | Hitchcock | 71/114 |

FOREIGN PATENT DOCUMENTS

| | | | |
|---|---|---|---|
| 969068 | 9/1964 | United Kingdom | 260/515 R |
| 1178400 | 1/1970 | United Kingdom | 260/515 R |

OTHER PUBLICATIONS

Casadio et al., Chem. Abst., 59, 1550(b), (1963).
Wagner et al., Syn. Org. Chem., John Wiley & Sons, New York, 412–415, (1965).
Marazzi-Uberti et al., Chem. Abst., 66, 114252(b), 1967.
Chatterjee et al., Tetrahedron Letters, No. 19, pp. 1683–1686, Pergamon Press, 1973.

*Primary Examiner*—James O. Thomas, Jr.
*Assistant Examiner*—G. T. Breitstein
*Attorney, Agent, or Firm*—H. G. Jackson

[57] ABSTRACT

This invention relates to α-(branched $C_3$–$C_4$ alkyl)naphthaleneacetic acids and a method for the control of undesirable plant species therewith. The invention also relates to a method for the preparation of the compounds.

3 Claims, No Drawings

BRANCHED ALKYL-2-NAPHTHALENEACETIC ACIDS AS HERBICIDES AND INSECTICIDE INTERMEDIATES

CROSS REFERENCE TO RELATED APPLICATION

Our copending application Ser. No. 673,244 filed of even date, now U.S. Pat. No. 4,046,799, discloses the use of the compounds of this invention as intermediates for the manufacture of substituted-benzyl $\alpha$-$C_1$-$C_4$ alkyl-2-naphthaleneacetate insecticides.

BACKGROUND OF THE INVENTION

1. Field of the Invention

The invention pertains to new chemical compounds which are useful herbicides and intermediates for the manufacture of insecticides.

2. Description of the Prior Art

British Pat. No. 969,068 (1964) discloses $\alpha$-substituted 1-naphthylacetic acids and pharmaceutical compositions containing those compounds. Acidi Naftilacetici-by Casadio, Pala, Bruzzese, Marazzi Uberti, Farmaco Edizione Scientifica 17: 797–817 (1962); 1-Naphthylacetic and 2-naphthylacetic acid derivatives; studies on the relationship between chemical structure and choleretic activity, Marazzi-Uberti, Turb and Bianchi, Research Laboratories of Istituo DeAngeli, Milan, Italy (1966); condensed aromatic compounds 1549 (1963) and 16025 (1964) and Chemical Abstracts 16027, Vol. 61.

SUMMARY OF THE INVENTION

This invention relates to novel 2-naphthaleneacetic acid compounds having the structure:

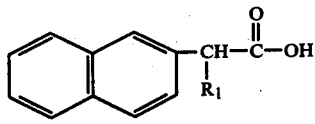

wherein $R_1$ represents a branched $C_3$-$C_4$ alkyl group, such as isopropyl, isobutyl, secondary butyl or tertiary butyl. The invention also relates to a method for the preemergence control of undesirable plant species by applying to soil containing seeds of the undesirable plants, a herbicidally effective amount of the active $\alpha$-branched $C_3$-$C_4$ alkyl-2-naphthaleneacetic acid. The invention further relates to a method for preparing the above defined branched alkyl-2-naphthaleneacetic acid compounds.

DETAILED DESCRIPTION

In accordance with this invention, alkylated-2-naphthaleneacetic acids represented by the formula:

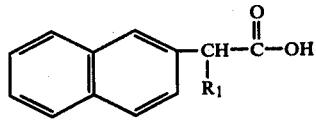

wherein, $R_1$ is a branched $C_3$-$C_4$ alkyl can be prepared by reacting approximately equimolar amounts of 2-naphthaleneacetonitrile and an alkyl halide represented by the formula: $R_1X$, wherein $R_1$ is isopropyl, isobutyl or sec-butyl, and X is halogen, such as chloro, iodo or bromo. An excess of the alkylhalide may of course, be used. This reaction is conducted in the presence of an anhydrous ammoniacal base and an aprotic solvent and yields the alkylated-2-naphthaleneacetonitrile which is readily converted, by means of hydrolysis, to the corresponding alkylated-2-naphthaleneacetic acid. The hydrolysis step can be carried out with a strong mineral acid and water at an elevated temperature, preferably a temperature between 120° C. and 150° C.

The reactions can be graphically illustrated as follows:

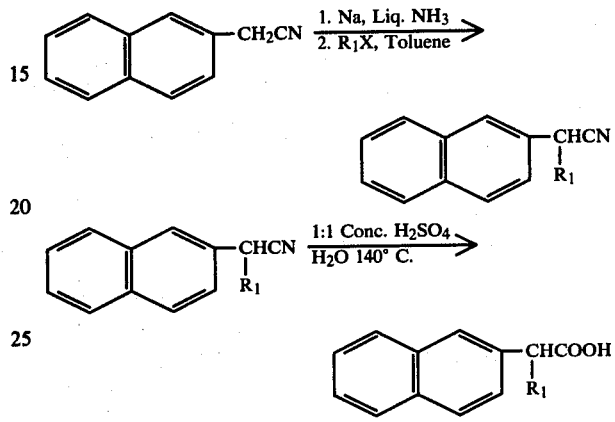

wherein $R_1$ is isopropyl, isobutyl or sec-butyl and X is halogen, preferably chloro or bromo.

The preparation of $\alpha$-tert-butyl-2-naphthaleneacetonitrile is carried out using 2-naphthaldehyde by the following sequence of reactions (1) reaction with t-butyl magnesium chloride, (2) conversion of the neopentyl alcohol to the chloride using thionyl chloride, (3) preparation of the Grignard reagent with magnesium in tetrahydrofuran, and, (4) carboxylation with carbon dioxide.

Typical aprotic solvents which can be employed in the alkylation of 2-naphthaleneacetonitrile include toluene, xylenes, benzene, diethyl ether, methylethyl ether, dimethoxyethane and the like.

The above-said alkylation can be conducted with commercially available sodium amide in the presence of an aprotic solvent, or it can be conducted with an alkali metal such as sodium or potassium in the presence of liquid ammonia and an aprotic solvent. The alkylation reaction may also be carried out using bases such as sodium or potassium alkoxides, preferably sodium or potassium t-butoxide. These reactions are preferably conducted at a temperature between 38° C. and 120° C.

The above-described alkylations of 2-naphthaleneacetonitrile with an alkyl halide represented by the formula, $R_1 X$, wherein $R_1$ is isopropyl, isobutyl, or sec-butyl, and X is halogen, such as chloro, bromo, or iodo, can also be carried out using aqueous sodium or potassium hydroxide as a base in the presence of crown ethers such as dicyclohexyl-18-crown-6, dibenzo-18-crown-6 and the like. These reactions are carried out at room temperature even though slightly elevated temperatures can lead to shorter reaction time. Solvents such as benzene, toluene and the like are employed for the dissolution of the starting 2-naphthaleneacetonitrile. The ratio of the catalyst (i.e., the crown ether) to the substrate ranges from 1.0 to 10.0 mole percent while that of the alkyl halide, is from 100 to 300 mole percent.

Typical acids which can be employed in the conversion of the alkylated-2-naphthaleneacetonitrile to the corresponding acid, are sulfuric acid, hydrochloric acid, phosphoric acid, glacial acetic acid and mixtures thereof. For the conversion, the presence of water in the reaction mixture is essential and we have found that the reaction appears to proceed satisfactorily only at elevated temperatures and preferably between 120° C. and 150° C. Somewhat, higher or lower temperatures may be used, but excessive temperatures cause charring of the reaction mixture and at low temperatures the reaction does not proceed at an acceptable rate.

The compounds of the present invention are useful as preemergence herbicidal agents. They are effective for the control of several undesirable broadleaf plants such as sesbania, mustard, pigweed and ragweed and likewise may be used for the control of undesirable grasses such as barnyardgrass, crabgrass and foxtails.

Advantageously, the compounds of this invention are also useful as intermediates for the preparation of highly effective insecticidal agents.

The said insecticidal agents can be obtained by reaction of the alkylated-2-naphthaleneacetic acid with a thionyl halide such as thionyl chloride or thionyl bromide or a phosphorus halide such as phosphorus trichloride, phosphorus tribromide or phosphorus pentachloride, in the presence of an organic solvent such as methylene chloride, toluene, benzene, or the like. The halide and acid are employed in approximately equimolar amounts, although as much as 2 mole equivalents of the halide, per mole of the acid, may be used. The reaction is preferably conducted at about the refluxing temperature of the solvent, generally between about 40° C. and 110° C. The alkylated-2-naphthaleneacetyl halide is then reacted with the appropriate m-phenoxybenzyl alcohol to obtain the insecticidal agent. This reaction is usually carried out with equimolar amounts of the alcohol and the alkylated-2-naphthaleneacetyl halide in the presence of an inert hydrocarbon solvent and a base such as aqueous sodium hydroxide, pyridine, or triethylamine.

Preparation of insecticidal agents from the alkylated-2-naphthaleneacetic acid may be graphically illustrated as follows:

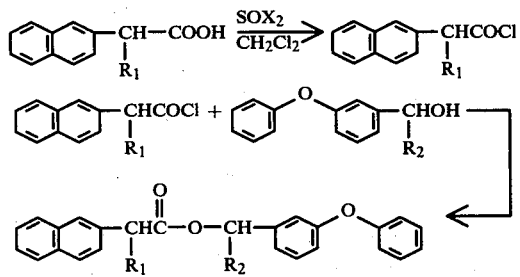

wherein R₁ is a branched C₃-C₄ alkyl and R₂ is H or CN.

As indicated above, the alkylated-2-naphthaleneacetic acid compounds of this invention are effective for the control of a wide variety of undesirable broadleaf and grass plants when applied to soil containing seeds or propagating organs of said plants. In practice it is generally desirable to apply the active compound in sufficient amount to provide from about 2.24 to 11.2 kg/hectare thereof and such application may be in the form of a liquid or solid formulation.

The compounds of the invention may be prepared as wettable powders, flowable liquids, emulsifiable or water miscible concentrates, dusts, granular particles or the like.

Dusts are generally prepared by grinding together about 1% to 25% by weight of the active agent with from about 99% to 75% by weight of a solid diluent such as kaolin, attapulgite, diatomaceous earth, or the like. Dust concentrates are prepared in similar fashion excepting that about 25% to 95% by weight of the active compound is ground with about 75% to 5% by weight of the diluent.

Wettable powders are prepared in the same manner as the dust concentrates excepting that about 1% to 5% by weight of a dispersing agent such as sodium lignosulfonate, or the sodium salt of condensed naphthalene sulfonic acid is blended with the mixture and about 1% to 5% of a surfactant is also blended with the formulation.

In practice, the wettable powder is dispersed in water and applied as a liquid spray to soil in the area or locus in which control of undesirable plants is sought.

Water-miscible concentrates are prepared by dissolving from 15% to 95% of the active compound in 85% to 5% of a water-miscible solvent, such as water itself or another polar water-miscible solvent, such as 2-methoxyethanol, methanol, propylene glycol, diethylene glycol, diethylene glycol monoethyl ether, formamide and dimethylformamide. Application of the material is made by adding a predetermined quantity of the water-miscible concentrate to a spray tank and applying the mixture as such or in combination with a suitable diluent, such as a further quantity of water or one of the above polar solvents. Generally, addition of a surfactant to the mixture is also desirable.

The surfactant is preferably a nonionic surfactant such as an alkylphenol ethylene oxide condensate, and is used at the level of about 0.17% to 5% by volume.

This invention is further illustrated by the examples setforth below.

EXAMPLE 1

Preparation of α-Isopropyl-2-naphthaleneacetonitrile

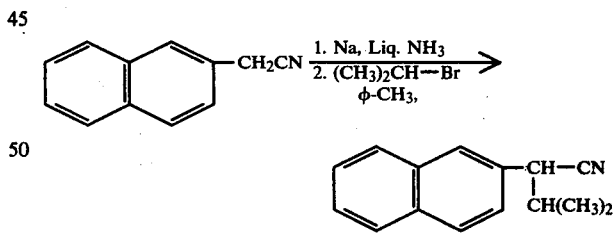

Anhydrous liquid ammonia (700 ml) is introduced through an inlet tube into a 4-necked flask equipped with a cold-finger condenser (dry ice-isopropanol trap) and a mechanical stirrer. A few crystals of hydrated ferric nitrate are added and sodium (34.2 g, 1.485 mole) is added in small portions over a 1 hour period. The reaction mixture is stirred for 30 minutes to dissolve all the sodium. When the blue color changes to gray completely, a solution of 2-naphthaleneacetonitrile (225.7 g, 1.35 mole) in toluene (800 ml) is then added carefully over a 2½ hour period. The cold-finger condenser is replaced by an ordinary condenser (no water flow) and the red-brown reaction mixture is allowed to stir overnight with loss of most of the ammonia. The last traces of ammonia are removed by heating the reaction mixture to 55° C. 2-Bromopropane (189.0 g, 1.54 mole) is then added at 55° C. to 60° C. over 2 hour period. This treatment requires no external heating. After the addition, the reaction mixture is refluxed for 3 hours and cooled to room temperature. The reaction mixture is admixed with water (800 ml) and the organic phase is separated from the aqueous phase. The aqueous phase is extracted twice with benzene (2×150 ml). The combined organic phases are then washed with water, saturated sodium chloride and then evaporated to an oil (312 g). Vacuum distillation gives the product: α-isopropyl-2-naphthaleneacetonitrile, (264.3, 94%); b.p. 137° (0.2 mm).

This procedure is repeated in all essential details excepting that isobutyl bromide (1-bromo-2-methylpropane) is substituted for 2-bromopropane. This latter procedure yields α-isobutyl-2-naphthaleneacetonitrile. When the procedure is repeated with sec-butylbromide the corresponding α-sec-butyl-2-naphthaleneacetonitrile is obtained.

EXAMPLE 2

Preparation of α-sec-butyl-2-naphthaleneacetonitrile

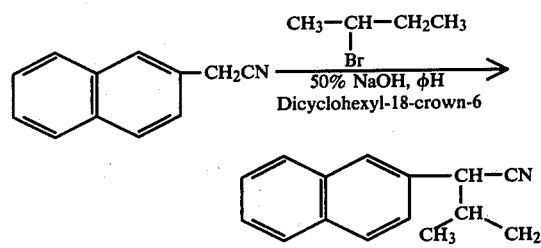

A mixture of 2-naphthaleneacetonitrile (30.00 g, 0.179 mole), dicyclohexyl-18-crown-6 [1.60 g, 0.0043 mole (2.4 mole %)], 2-bromobutane (50.20 g, 0.366 mole), benzene (80 ml) and sodium hydroxide solution (50%, 80 ml) is stirred at room temperature for 16 hours. The organic layer is diluted with ether (250 ml), separated, washed successively with water, dilute hydrochloric acid and water and dried over sodium sulfate. Evaporation and distillation under vacuum gives α-sec-butyl-2-naphthaleneacetonitrile (34.3 g, 86%); b.p. 130° C. (0.1 mm).

Analysis calculated for $C_{16}H_{17}N$: C, 86.05; H, 7.68; N, 6.27. Found: C, 85.91; H, 7.76; N, 5.96.

EXAMPLE 3

Preparation of α-isobutyl-2-naphthaleneacetonitrile

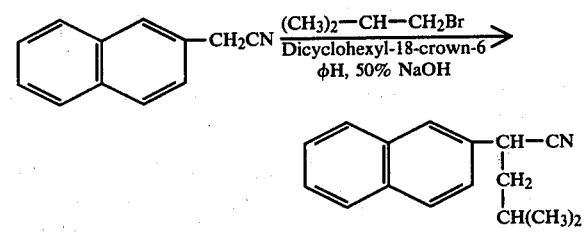

Using isobutyl bromide instead of sec-butyl bromide and 5.8 mole percent of dicyclohexyl-18-crown-6 in Example 3 repetition of the above experiment gives α-isobutyl-2-naphthaleneacetonitrile in 79% yield; b.p. 120°–130° C. (0.025 mm).

EXAMPLE 4

Preparation of α-Isopropyl-2-naphthaleneacetic acid

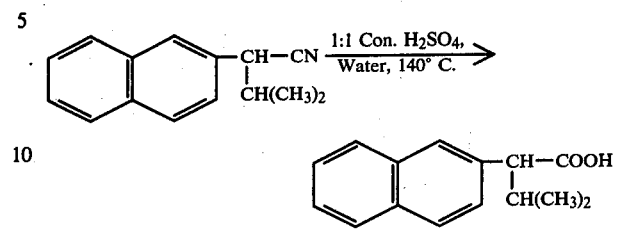

A mixture of α-isopropyl-2-naphthaleneacetonitrile (264.3 g, 1.263 mole) in concentrated sulfuric acid (660 ml) and water (660 ml) is heated at 140° C. for 12 hours. The mixture is allowed to cool slowly during which the acid precipitates. The solid is collected by filtration, washed thoroughly with cold water (4×500 ml), and dried in a vacuum oven at 50° C. The yield is 281 g (97.6%). The solid is taken up in hexane (750 ml) and benzene (750 ml) and brought to boiling. The cloudy solution on cooling gives a white crystalline solid, which is collected and dried; (227 g, 2 crops, 78.8%); m.p. 129°–130° C. An analytical sample prepared in another run has a m.p. 130°–131° C.

Analysis: Calculated for $C_{15}H_{16}O_2$ (228.18): C, 78.92; H, 7.06. Found: C, 79.12; H, 7.30.

Following the above-procedure but substituting α-isobutyl-2-naphthaleneacetonitrile or α-sec-butyl-2-naphthaleneacetonitrile for α-isopropyl-2-naphthaleneacetonitrile yields respectively, α-isobutyl-2-naphthaleneacetic acid melting point 115° C. to 119° C. and α-sec-butyl-2-naphthaleneacetic acid, melting point 112° C. to 115° C.

EXAMPLE 5

Preparation of α-Isopropyl-2-naphthylacetyl chloride

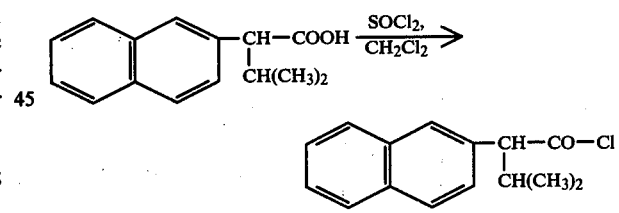

A suspension of α-isopropyl-2-naphthaleneacetic acid (205.5 g, 0.90 mole) in methylene chloride (1500 ml and thionyl chloride (119.0 g, 1.0 mole) is gently refluxed for 20–22 hours. The clear brown solution is evaporated at 45°–50° C. using a water aspirator to give the crude acid chloride (219 g, 98.6%), which is used as such for esterification.

EXAMPLE 6

Preparation of α-Cyano-m-phenoxybenzyl α-isopropyl-2-naphthaleneacetate

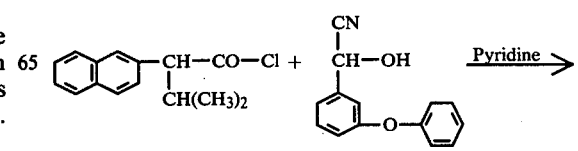

-continued

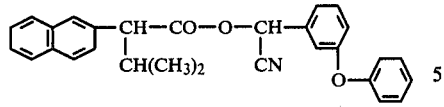

A solution of α-isopropyl-2-naphthlyacetyl chloride (219 g, 0.887 mole) in benzene (350 ml) is added to a solution of α-cyano-m-phenoxybenzyl alcohol (179.8 g, 0.798 mole) and pyridine (70.2 g, 0.887 mole) in ether (750 ml) at 0°–10° C. over a 1½ hour period. Pyridine hydrochloride precipitates out during the addition. The reaction mixture, after stirring overnight at room temperature, is diluted with more ether (500 ml) and poured into water (1200 ml). The organic phase is separated, washed with water, 10% $H_2SO_4$ and water and dried over $Na_2SO_4$. Evaporation gives an orange-brown gum (348 g, 100% crude yield, 87.5% pure by liquid chromatography).

A sample purified by chromatography on silica gel is analyzed. Calculated for $C_{29}H_{25}NO_3$: C, 79.98, H, 5.79; N, 3.22. Found: C, 79.88; H, 5.89; N, 3.12.

The thus prepared α-cyano-m-phenoxybenzyl α-isopropyl-2-naphthaleneacetate is a highly effective insecticidal agent. Similarly, the corresponding α-cyano-m-phenoxybenzyl α-isobutyl and α-sec-butyl-2-naphthaleneacetates are also useful as insecticidal agents. Additionally, it is noted that m-phenoxybenzyl α-isopropyl-2-naphthleneacetate and the corresponding m-phenoxybenzyl α-isobutyl and α-sec-butyl-2-naphthaleneacetates, are likewise effective insecticidal agents.

The latter compounds are prepared as above-indicated, excepting that m-phenoxybenzyl alcohol is substituted for α-cyano-m-phenoxybenzyl alcohol. Analysis for m-phenoxybenzyl α-isopropyl-2-naphthaleneacetate is as follows: Calculated: C, 81.92; H, 6.39. Found : C, 81.66; H, 6.46.

EXAMPLE 7

Preemergence Herbicidal Evaluation

The preemergence activity of the compounds of the present invention is demonstrated by the following tests wherein a 50/50 acetone/water mixture and sufficient test compound to provide from 4 to 10 pounds per acre, or 4.48 to 11.2 kg/hectare, is applied to pots planted with seeds of test plant species.

The pots are prepared the day of herbicide treatment by putting 100 ml of soil in each plastic pot as a base.

Seeds of each of the plant species identified below are then separately mixed with soil and 50 ml of the soil seed mix added to the pot. The pots are then tamped to level the soil and the soil is prewetted with water prior to herbicide application. This prewetting insures that the herbicide treatment solution spreads evenly over the surface of the pot and protects the weed seeds from acetone injury. Each of the weed species is contained in a separate pot. The pots are then arranged in 10×12 inch flats prior to chemical treatment.

To obtain the 11.2 kg/ha rate, the planted pots are treated with 5 ml of test solution and then placed on benches in the greenhouse. The 4.48 kg/ha rate is obtained by spraying the planted pots. After spraying the pots are placed in the greenhouse. Pots are watered after treatment and held in the greenhouse for 3 weeks at which time the results are recorded, as reported below in Table I.

| Plant Species Used in Preemergence Herbicide Evaluation | | |
|---|---|---|
| Common Name | Abbreviation | Scientific Name |
| Wild Mustard | MU | Brassica kaber |
| Pigweed | PI | Amaranthus retroflexus |
| Ragweed | RW | Ambrosia artemisiifolia |
| Morningglory | MG | Ipomoea purpurea |
| Barnyardgrass | BA | Echinochloa crusgalli |
| Crabgrass | CR | Digitaria sanguinalis |
| Green Foxtail | FO | Setaria viridis |
| Wild Oats | WO | Avena fatua |
| Sesbania | SE | Sesbania exaltata |
| Tea Weed | TW | Sida spinosa |
| Corn | CN | Zea mays |
| Cotton | CO | Gossypium hirsutum |
| Soybean | SY | Glycine max |
| Rice | RI | Oryza sativa |
| Velvetleaf | VL | Abutilon theophrasti |

The rating system used in these tests is reported below.

| Rating System: | % Difference in Growth from the Check[*1] |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |
| 4 - Abnormal growth, that is, a definite physiological malformation but with an over-all effect less than a 5 on the rating scale. | |

[*1]Based on visual determination of stand, size, vigor, chlorosis growth malformation and over-all plant appearance.

Table I

| | | Preemergence Herbicidal Activity of Test Compounds Plant Species | | | | | | | | | | | | | |
|---|---|---|---|---|---|---|---|---|---|---|---|---|---|---|---|
| | Rate | Broadleaf Weeds | | | | | | | Grass Weeds | | | Crops | | | |
| Compound | kg/ha | SE | MU | PI | RW | MG | TW | VL | BA | CR | FO | CN | CO | SY | RI |
| α-Isopropyl-2-naphthylene- | 11.2 | 9 | 9 | 9 | 7 | 0 | 9 | 8 | 8 | 9 | 9 | | | | |
| acetic acid | 4.48 | 9 | 0 | 9 | 5 | 0 | 7 | 6 | 7 | 4 | 3 | 0 | 2 | 2 | 3 |

What is claimed is:

1. The compound α-isopropyl-2-naphtheneacetic acid.

2. A method for the preemergence control of undesirable plant species comprising applying to soil containing seeds or propagating organs thereof, a herbicidally effective amount of the compound α-isopropyl-2-naphthaleneacetic acid.

3. A method according to claim 2 wherein the compound is applied at the rate of 4.48 to 11.2 kg/hectare.

* * * * *